(12) United States Patent
Richard

(10) Patent No.: US 10,729,435 B2
(45) Date of Patent: Aug. 4, 2020

(54) ADAPTER ASSEMBLIES FOR INTERCONNECTING SURGICAL LOADING UNITS AND HANDLE ASSEMBLIES

(71) Applicant: Covidien LP, Mansfield, MA (US)

(72) Inventor: Paul Richard, Shelton, CT (US)

(73) Assignee: COVIDIEN LP, Mansfield, MA (US)

( * ) Notice: Subject to any disclaimer, the term of this patent is extended or adjusted under 35 U.S.C. 154(b) by 779 days.

(21) Appl. No.: 15/292,383

(22) Filed: Oct. 13, 2016

(65) Prior Publication Data
US 2017/0128069 A1     May 11, 2017

Related U.S. Application Data

(60) Provisional application No. 62/251,863, filed on Nov. 6, 2015.

(51) Int. Cl.
*A61B 17/072*     (2006.01)
*A61B 17/00*     (2006.01)
(Continued)

(52) U.S. Cl.
CPC ............ *A61B 17/07207* (2013.01); *A61B 2017/0046* (2013.01); *A61B 2017/00398* (2013.01);
(Continued)

(58) Field of Classification Search
USPC ........................................ 227/180.1
See application file for complete search history.

(56) References Cited

U.S. PATENT DOCUMENTS 2,777,340 A    1/1957   Hettwer et al.
2,957,353 A    10/1960   Babacz
(Continued)

FOREIGN PATENT DOCUMENTS

AU    2008229795 A1    4/2009
CA    2451558 A1    1/2003
(Continued)

OTHER PUBLICATIONS

European Search Report dated Mar. 31, 2017, corresponding to European Application No. 16197359.9; 8 pages.
(Continued)

*Primary Examiner* — Michelle Lopez
*Assistant Examiner* — Chinyere J Rushing-Tucker
(74) *Attorney, Agent, or Firm* — Carter, DeLuca & Farrell LLP

(57) ABSTRACT

An adapter assembly includes an elongated body, a switch, a sensor link, and an annular member. The elongated body includes a distal portion configured to couple to a surgical loading unit. The distal portion defines a slot therein. The sensor link has a proximal end disposed adjacent the switch and a distal end disposed adjacent the distal portion of the elongated body. The sensor link is longitudinally movable between a proximal position and a distal position. The annular member has a protrusion movably disposed within the slot. The annular member is rotatable between a first orientation, in which the annular member prevents movement of the sensor link to the distal position, and a second orientation, in which the sensor link moves distally to toggle the switch. The annular member is resiliently biased toward the first orientation.

20 Claims, 9 Drawing Sheets

(51) Int. Cl.
*A61B 90/00* (2016.01)
*A61B 17/29* (2006.01)

(52) U.S. Cl.
CPC .............. *A61B 2017/00473* (2013.01); *A61B 2017/00477* (2013.01); *A61B 2017/07257* (2013.01); *A61B 2017/07271* (2013.01); *A61B 2017/07285* (2013.01); *A61B 2017/2903* (2013.01); *A61B 2090/0808* (2016.02)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,865,361 A * | 2/1999 | Milliman ......... A61B 17/07207 227/176.1 |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |

(56) References Cited

U.S. PATENT DOCUMENTS

| | | |
|---|---|---|
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,896 B2 | 10/2010 | Racenet |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0083808 A1* | 4/2008 | Scirica ............ A61B 17/07207 227/175.1 |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |

(56) References Cited

U.S. PATENT DOCUMENTS

| | | |
|---|---|---|
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0206131 A1* | 8/2009 | Weisenburgh, II ............ A61B 17/07207 227/175.2 |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0074063 A1* | 3/2011 | Scirica ............. A61B 17/07207 264/265 |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0092719 A1* | 4/2013 | Kostrzewski .... A61B 17/07207 227/177.1 |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1* | 12/2013 | Nicholas ............... A61B 17/068 606/1 |
| 2013/0324979 A1* | 12/2013 | Nicholas ............... A61B 17/068 606/1 |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1* | 1/2014 | Snow ............... A61B 17/07207 606/130 |
| 2014/0025046 A1 | 1/2014 | Williams et al. |
| 2014/0027491 A1* | 1/2014 | Beardsley ........ A61B 17/07207 227/175.1 |
| 2014/0110455 A1 | 4/2014 | Ingmanson et al. |
| 2014/0207125 A1 | 7/2014 | Applegate et al. |
| 2014/0207182 A1* | 7/2014 | Zergiebel ............ A61B 17/2841 606/205 |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0316431 A1 | 11/2015 | Collins et al. |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 a1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2668912 A2 | 12/2013 |

(56) References Cited

FOREIGN PATENT DOCUMENTS

| | | |
|---|---|---|
| EP | 2676615 A2 | 12/2013 |
| EP | 2684529 A2 | 1/2014 |
| EP | 2807984 A2 | 12/2014 |
| ES | 2333509 A1 | 2/2010 |
| JP | 08-038488 | 2/1996 |
| JP | 2005-125075 A | 5/2005 |
| KR | 20120022521 A | 3/2012 |
| WO | 99/15086 A1 | 4/1999 |
| WO | 2000/072760 A1 | 12/2000 |
| WO | 2000/072765 A1 | 12/2000 |
| WO | 2003/000138 A2 | 1/2003 |
| WO | 2003/026511 A1 | 4/2003 |
| WO | 2003/030743 A2 | 4/2003 |
| WO | 2003065916 A1 | 8/2003 |
| WO | 2003/077769 A1 | 9/2003 |
| WO | 2003/090630 A2 | 11/2003 |
| WO | 2004/107989 A1 | 12/2004 |
| WO | 2006/042210 A2 | 4/2006 |
| WO | 2007016290 A2 | 2/2007 |
| WO | 2007/026354 A1 | 3/2007 |
| WO | 2007137304 A2 | 11/2007 |
| WO | 2008/131362 A2 | 10/2008 |
| WO | 2008/133956 A2 | 11/2008 |
| WO | 2009/039506 A1 | 3/2009 |
| WO | 2007014355 A3 | 4/2009 |
| WO | 2009/132359 A2 | 10/2009 |
| WO | 2009/143092 A1 | 11/2009 |
| WO | 2009/149234 A1 | 12/2009 |
| WO | 2011/108840 A2 | 9/2011 |
| WO | 2012/040984 A1 | 4/2012 |

OTHER PUBLICATIONS

Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.

* cited by examiner

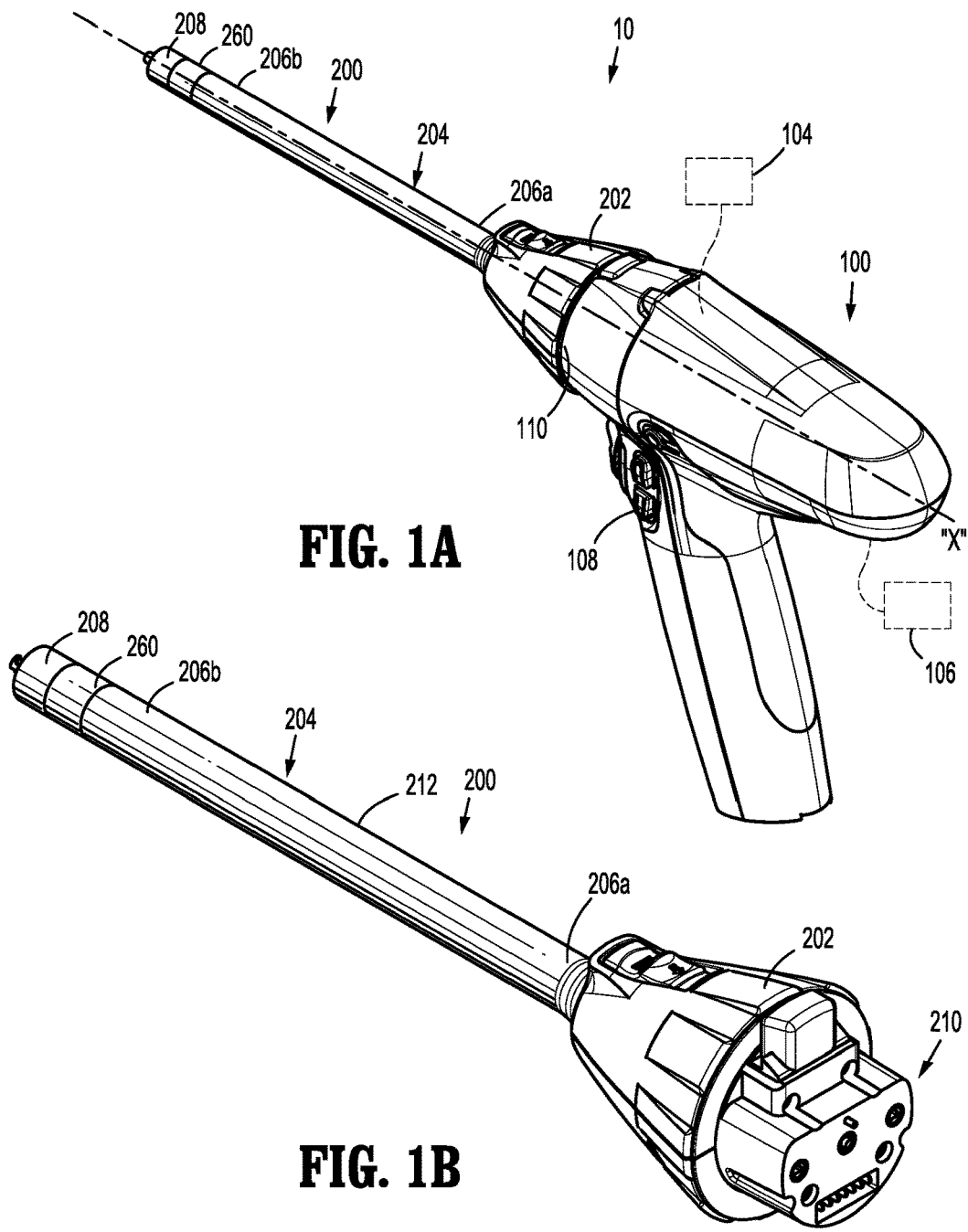
FIG. 1A
FIG. 1B
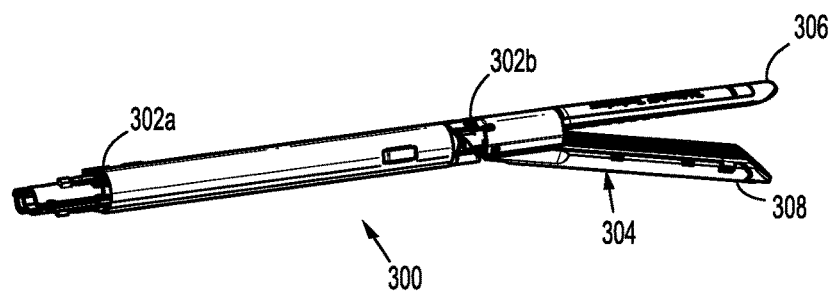
FIG. 1C

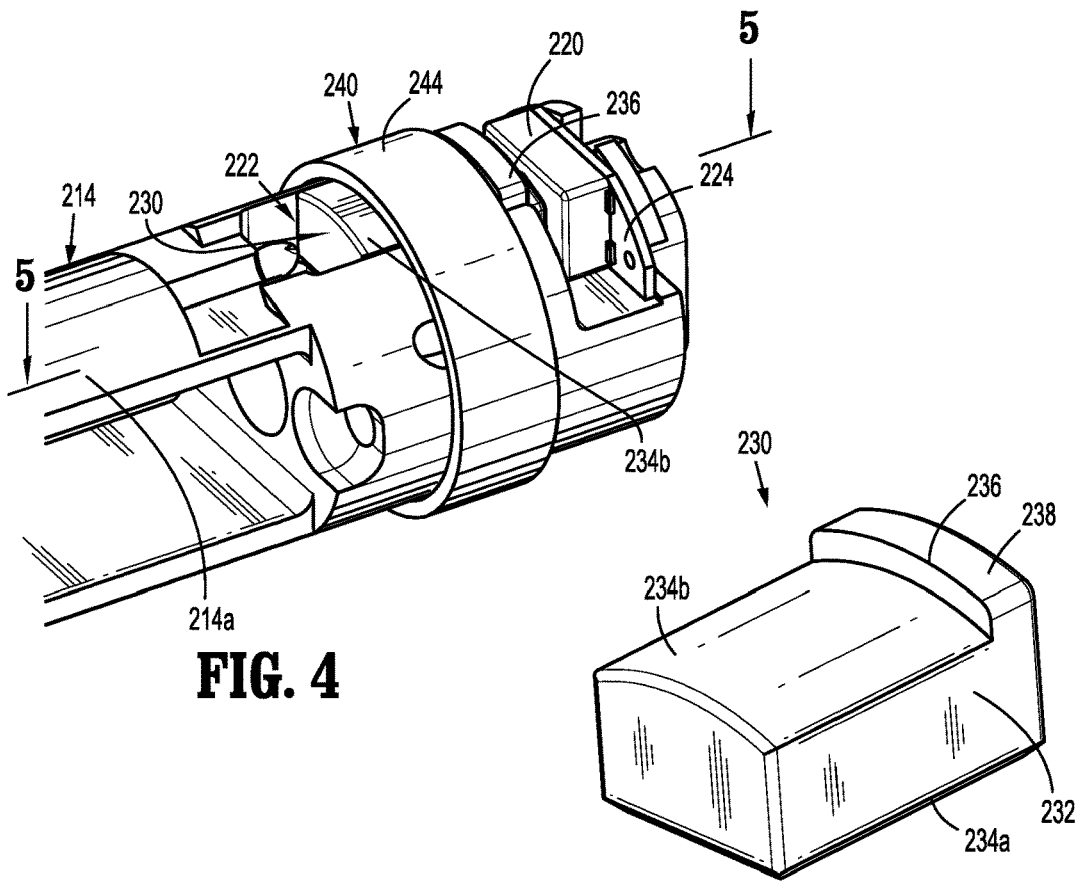
FIG. 4
FIG. 3
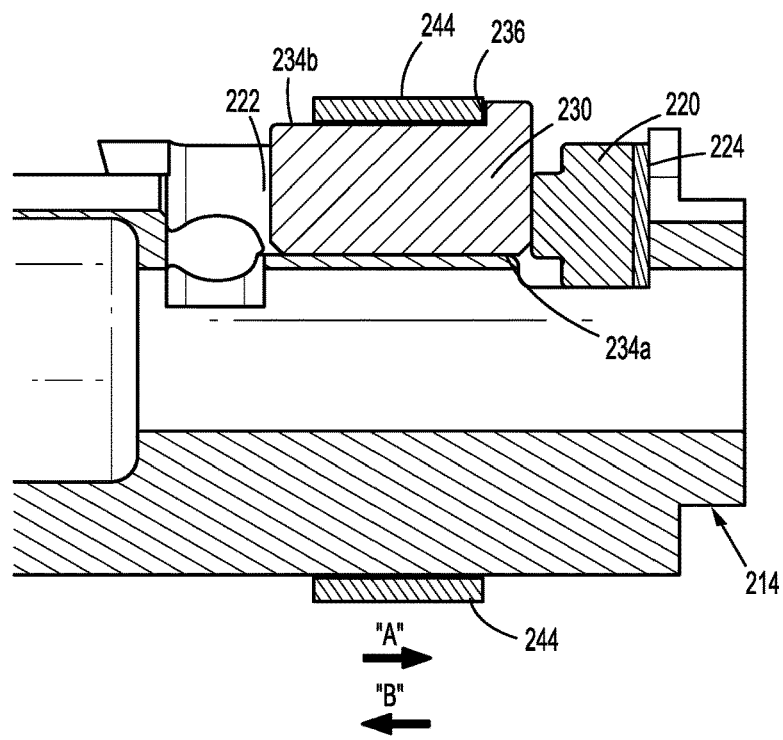
FIG. 5

ADAPTER ASSEMBLIES FOR INTERCONNECTING SURGICAL LOADING UNITS AND HANDLE ASSEMBLIES

CROSS-REFERENCE TO RELATED APPLICATIONS

This application claims the benefit of and priority to U.S. Provisional Patent Application No. 62/251,863 filed Nov. 6, 2015, the entire disclosure of which is incorporated by reference herein.

BACKGROUND

1. Technical Field

The present disclosure relates to adapter assemblies for use with an electromechanical surgical system and their methods of use. More specifically, the present disclosure relates to hand-held, electromechanical surgical instruments capable of detecting the presence of a loading unit and/or identifying one or more parameters of a loading unit attached to an adapter assembly.

2. Background of Related Art

Linear clamping, cutting, and stapling surgical devices may be employed in surgical procedures to resect tissue. Conventional linear clamping, cutting, and stapling devices include a handle assembly, an elongated shaft and a distally located surgical loading unit. The loading unit includes a pair of gripping members, which clamp about tissue to be stapled. One of the gripping members includes a staple cartridge receiving region and a mechanism for driving the staples up through tissue and against an anvil portion on the other gripping member.

In many instances, the handle assembly is reusable and the loading unit is disposable. The disposable loading unit may be selectively coupled to the handle assembly via an adapter assembly prior to use and then disconnected from the adapter assembly and therefore decoupled from the reusable handle assembly following use in order to be disposed of or in some instances sterilized for re-use.

A need exists for various types of adapter assemblies that communicate relevant information to a handle assembly of a surgical instrument upon a proper coupling of a loading unit with the handle assembly.

SUMMARY

The present disclosure relates to adapter assemblies for use between handle assemblies and loading units. The present disclosure also relates to mechanisms for toggling a switch of an adapter assembly for effectively communicating information about a loading unit to a handle assembly, which is coupled to the adapter assembly, upon engagement of the loading unit with the handle assembly.

In an aspect of the present disclosure, an adapter assembly is provided. The adapter assembly includes an elongated body, a switch disposed within the elongated body, a sensor link, and an annular member. The elongated body includes a proximal portion configured to couple to a handle assembly and a distal portion configured to couple to a surgical loading unit. The sensor link has a proximal end disposed adjacent the switch and a distal end disposed adjacent the distal portion of the elongated body. The sensor link is longitudinally movable between a proximal position and a distal position. The annular member is disposed within the distal portion of the elongated body and is rotatable between a first orientation, in which the annular member prevents movement of the sensor link to the distal position, and a second orientation, in which the sensor link is movable from the proximal position to the distal position to toggle the switch, the annular member being resiliently biased toward the first orientation.

In embodiments, the distal portion of the elongated body may define a slot therein and the annular member may include a protrusion movably disposed within the slot. The distal portion of the elongated body may include a biasing member disposed within the slot and in abutment with the protrusion of the annular member. The slot of the elongated body may extend circumferentially about the distal portion thereof.

In embodiments, the annular member may include an appendage defining a cavity therein configured to capture a surface feature of the surgical loading unit. The appendage may abut the distal end of the sensor link when the annular member is in the first orientation such that the appendage maintains the sensor link in the proximal position.

In embodiments, the elongated body may define a longitudinal channel within the proximal portion. The adapter assembly may further include a pusher movably disposed within the longitudinal channel. The proximal end of the sensor link may be in engagement with the pusher such that movement of the sensor link toward the distal position moves the pusher to actuate the switch. The pusher may include a stepped portion and the proximal end of the sensor link may include a ring abutting the stepped portion such that movement of the ring moves the pusher.

In embodiments, the sensor link may be resiliently biased toward the distal position.

In embodiments, the adapter assembly may further include a locking link disposed within the elongated body. The locking link may include an extension configured for locking engagement with a lug of the surgical loading unit. The locking link may be resiliently biased to secure the surgical loading unit to the distal portion of the elongated body upon insertion and rotation of the surgical loading unit into the elongated body.

In another aspect of the present disclosure, a surgical instrument is provided. The surgical instrument includes a handle assembly, a surgical loading unit, and an adapter assembly. The handle assembly includes a processor configured to control a motor. The surgical loading unit has a proximal end and a distal end. The proximal end has a surface feature and the distal end has an end effector. The adapter assembly includes an elongated body, a switch disposed adjacent the proximal portion of the elongated body, a sensor link, and an annular member. The elongated body includes a proximal portion configured to couple to the handle assembly and a distal portion configured to couple to the surgical loading unit. The distal portion defines a slot therein. The sensor link has a proximal end disposed adjacent the switch and a distal end disposed adjacent the distal portion of the elongated body. The sensor link is longitudinally movable between a proximal position and a distal position. The annular member has a protrusion movably disposed within the slot of the elongated body. The annular member is rotatable between a first orientation, in which the annular member prevents movement of the sensor link to the distal position, and a second orientation, in which the sensor link is movable from the proximal position to the distal position to toggle the switch. The annular member is resiliently biased toward the first orientation.

In embodiments, the processor may be configured to activate the motor upon the switch being toggled.

As used herein, the term "toggle" is defined as a transition between a first condition, which is one of an actuated state or an unactuated state of a switch, and a second condition, which is the other of the actuated or unactuated states of the switch.

BRIEF DESCRIPTION OF THE DRAWINGS

Embodiments of the present disclosure are described herein with reference to the accompanying drawings, wherein:

FIG. 1A is a perspective view of a handle assembly and an adapter assembly of a hand-held, electromechanical surgical instrument, in accordance with an embodiment of the present disclosure;

FIG. 1B is a perspective view of an embodiment of an adapter assembly of the surgical instrument of FIG. 1A;

FIG. 1C is a side view of a surgical loading unit of the surgical instrument of FIG. 1A, including an end effector attached thereto;

FIG. 3 is a perspective view of a pusher of the adapter assembly of FIG. 1B;

FIG. 4 is a perspective view of the proximal portion of the inner housing of FIG. 2, illustrating a switch, the pusher of FIG. 3, and a ring of a switch actuator assembled therein;

FIG. 5 is a cross-section, taken along line 5-5 in FIG. 4, illustrating the switch, the pusher, and the ring of the switch actuator;

DETAILED DESCRIPTION

Figure 2:
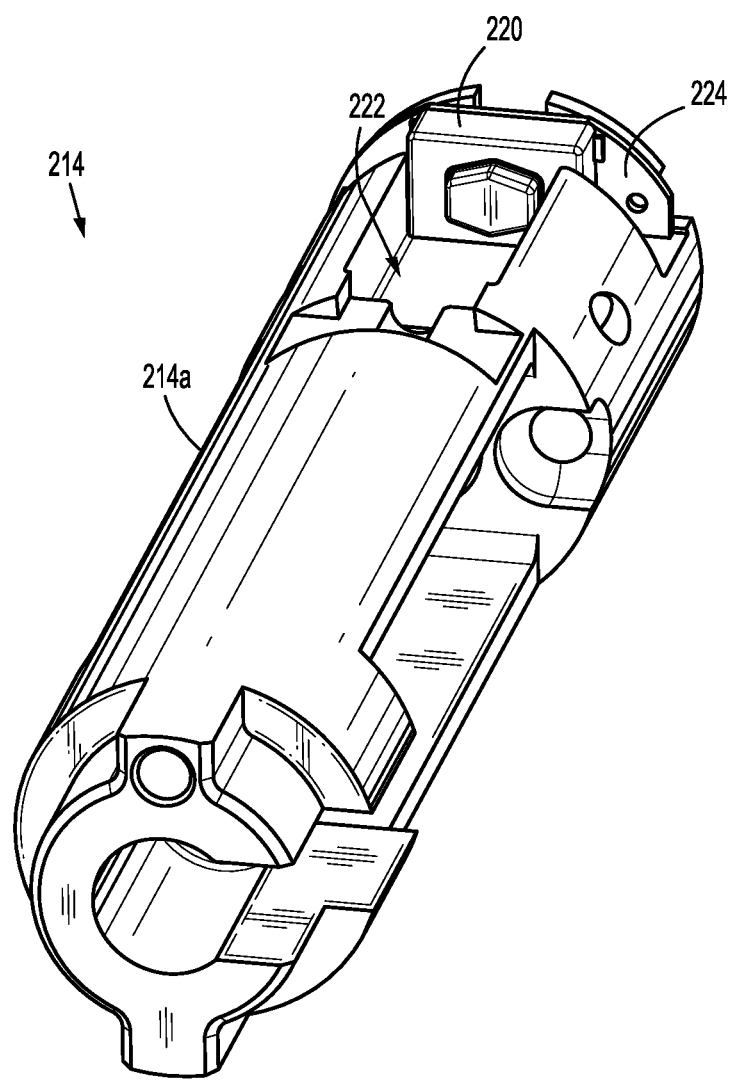
FIG. 2 is a perspective view of a proximal portion of an inner housing of the adapter assembly of FIG. 1B.

Embodiments of the presently disclosed surgical instruments, surgical loading units, and adapter assemblies for electromechanical surgical devices and/or handle assemblies are described in detail with reference to the drawings, in which like reference numerals designate identical or corresponding elements in each of the several views. As used herein, the term "distal" refers to that portion of the surgical instrument, adapter assembly, handle assembly, loading unit or components thereof, farther from the user, while the term "proximal" refers to that portion of the surgical instrument, adapter assembly, handle assembly, loading unit or components thereof, closer to the user.

With reference to FIGS. 1A-C, a surgical instrument, in accordance with an embodiment of the present disclosure, is generally designated as 10, and is in the form of a powered, hand-held, electromechanical surgical instrument including a handle assembly 100 configured for selective attachment thereto with any one of a number of adapter assemblies 200, and, in turn, each unique adapter assembly 200 is configured for selective connection with any number of surgical loading units 300. Loading unit 300 and adapter assembly 200 are configured for actuation and manipulation by handle assembly 100.

Reference may be made to International Publication No. WO 2009/039506 and U.S. Patent Application Publication No. 2011/0121049, the entire contents of all of which are incorporated herein by reference, for a detailed description of the construction and operation of an exemplary electromechanical, hand-held, powered surgical instrument.

Handle assembly 100 includes one or more controllers (not shown), a power source (not shown), a processor 104, and a drive mechanism having one or more motors 106, gear selector boxes (not shown), gearing mechanisms (not shown), and the like. Processor 104 is configured to control motors 106 and to detect a presence of a loading unit, for example, loading unit 300, and/or determine one or more parameters of loading unit 300, as described herein. Handle assembly 100 further includes a control assembly 108. Control assembly 108 may include one or more finger-actuated control buttons, rocker devices, joystick or other directional controls, whose input is transferred to the drive mechanism to actuate adapter assembly 200 and loading unit 300.

In particular, the drive mechanism is configured to drive shafts and/or gear components in order to selectively move an end effector 304 of loading unit 300 to rotate end effector 304 about a longitudinal axis "X" defined by surgical instrument 10 relative to handle assembly 100, to move a cartridge assembly 308 relative to an anvil assembly 306 of end effector 304, and/or to fire a stapling and cutting cartridge within cartridge assembly 308 of end effector 304.

With continued reference to FIG. 1A, handle assembly 100 defines a nose or connecting portion 110 configured to accept a corresponding drive coupling assembly 210 of adapter assembly 200 (FIG. 1B). Connecting portion 110 of handle assembly 100 has a cylindrical recess (not shown) that receives drive coupling assembly 210 of adapter assembly 200 when adapter assembly 200 is mated to handle assembly 100. Connecting portion 110 houses one or more rotatable drive connectors (not shown) that interface with corresponding rotatable connector sleeves of adapter assembly 200.

When adapter assembly 200 is mated to handle assembly 100, each of the rotatable drive connectors (not shown) of handle assembly 100 couples with a corresponding rotatable connector sleeve of adapter assembly 200. In this regard, the interface between a plurality of connectors of handle assembly 100 and a plurality of corresponding connector sleeves of the adapter assembly are keyed such that rotation of each of the drive connectors causes rotation of the corresponding connector sleeves of adapter assembly 200.

The mating of the drive connectors of handle assembly 100 with the connector sleeves of adapter assembly 200 allows rotational forces to be independently transmitted via each of the three respective connector interfaces. The drive connectors of handle assembly 100 are configured to be independently rotated by the drive mechanism.

Since each of the drive connectors of handle assembly 100 has a keyed and/or substantially non-rotatable interface with the respective connector sleeves of adapter assembly 200, when adapter assembly 200 is coupled to handle assembly 100, rotational force(s) are selectively transferred from drive mechanism of handle assembly 100 to adapter assembly 200.

The selective rotation of drive connector(s) of handle assembly 100 allows surgical instrument 10 to selectively actuate different functions of end effector 304. As discussed in greater detail below, selective and independent rotation of first drive connector of handle assembly 100 corresponds to the selective and independent opening and closing of end effector 304, and driving of a stapling/cutting component of end effector 304. Also, the selective and independent rotation of second drive connector of handle assembly 100 corresponds to the selective and independent articulation of end effector 304 about an articulation axis that is transverse to longitudinal axis "X." In particular, end effector 304 defines a second or respective longitudinal axis and is movable from a first position in which the second or respective longitudinal axis is substantially aligned with longitudinal axis "X" to at least a second position in which the second longitudinal axis is disposed at a non-zero angle with respect to longitudinal axis "X." Additionally, the selective and independent rotation of the third drive connector of handle assembly 100 corresponds to the selective and independent rotation of loading unit 300 about longitudinal axis "X" relative to handle assembly 100 of surgical instrument 10.

With continued reference to FIGS. 1A and 1B, adapter assembly 200 includes a knob housing 202 and an elongated body 204 extending from a distal end of knob housing 202. Knob housing 202 and elongated body 204 are configured and dimensioned to house the components of adapter assembly 200. Elongated body 204 may be dimensioned for endoscopic insertion. For example, elongated body 204 may be passable through a typical trocar port, cannula or the like. Knob housing 202 is dimensioned to not enter the trocar port, cannula of the like. Elongated body 204 has a proximal portion 206a attached to knob housing 202, which is configured to be attached to handle assembly 100. Elongated body 204 has a distal portion 206b configured to be coupled to proximal portion 302a of loading unit 300. Elongated body 204 includes a distal cap or tip 208 extending distally from distal portion 206b. It is contemplated that distal tip 208 may be detachably engaged to, integrally connected to, or monolithically formed with distal portion 206b.

Elongated body 204 includes a cylindrical outer housing 212 and a cylindrical inner housing 214 (FIGS. 2 and 8) disposed therein. Inner housing includes a switch 220 (FIG. 2), a pusher 230 (FIG. 3), a sensor link or switch actuator 240 (FIG. 6), an annular member 260 (FIGS. 1B and 9), and a locking link 280 (FIG. 10), each being disposed within or along inner housing 214.

With reference to FIG. 2, switch 220 is disposed adjacent proximal portion 206a of elongated body 204 and within a longitudinal channel 222 defined in a proximal portion 214a of inner housing 214. Switch 220 may be a depressible button mounted on a printed circuit board 224 that is electrically connected with processor 104 of handle assembly 100 or any other suitable toggle switch, e.g., a limit switch. Printed circuit board 224 extends transversely to inner housing 214 such that switch 220 is oriented in a proximal direction and along longitudinal axis "X." In embodiments, switch 220 may be oriented in any suitable direction, such as, for example, a distal direction or a lateral direction. Switch 220 is configured to toggle in response to a coupling of loading unit 300 to distal portion 206b of elongated body 204. Upon toggling of switch 220, switch 220 communicates to handle assembly 100 that loading unit 300 is lockingly engaged to distal portion 206b of elongated body 204 or that loading unit 300 is disengaged from distal portion 206b of elongated body 204, as described in further detail below.

With reference to FIGS. 3-5, proximal portion 214a of inner housing 214 further includes sliding member or pusher 230 movably disposed within longitudinal channel 222 thereof. Pusher 230 is configured to move/translate/slide within longitudinal channel 222 into and out of engagement with switch 220 in response to movement/translation/sliding of a ring 244 of switch actuator 240, as described in greater detail below. Pusher 230 has a rectangular body 232 having a substantially planar bottom surface 234a and an arcuate top surface 234b configured to be in flush engagement with ring 244 of switch actuator 240. Pusher 230 includes a lip or stepped portion 236 disposed at a distal end 238 thereof. Stepped portion 236 is in abutting engagement with ring 244 of switch actuator 240 such that distal movement of switch actuator 240 causes distal movement of pusher 230. In embodiments, pusher 230 may be connected to or integrally formed with ring 244 of switch actuator 240. In some embodiments, pusher 230 may be in the form of a projection or extension of ring 244 of switch actuator 240 that is configured to toggle switch 220 upon distal movement of switch actuator 240.

Figure 6:
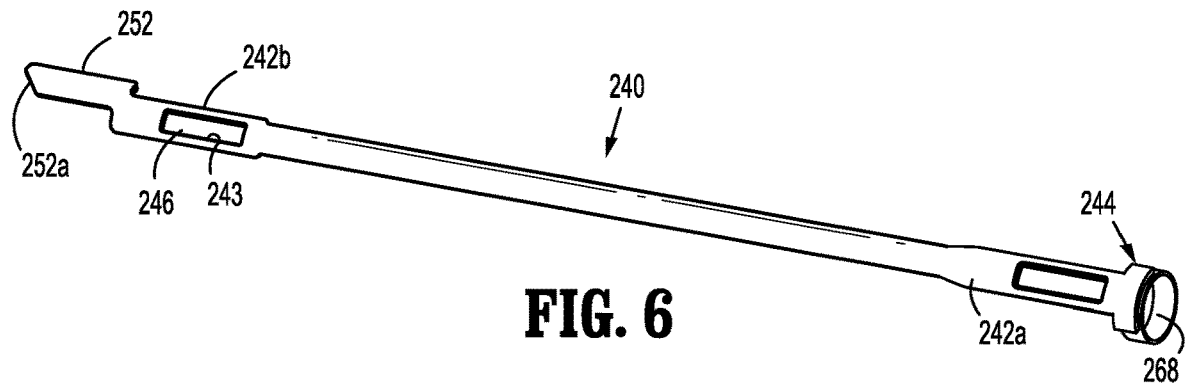
FIG. 6 is a perspective view of the switch actuator of the adapter assembly of FIG. 1B.
Figure 7:
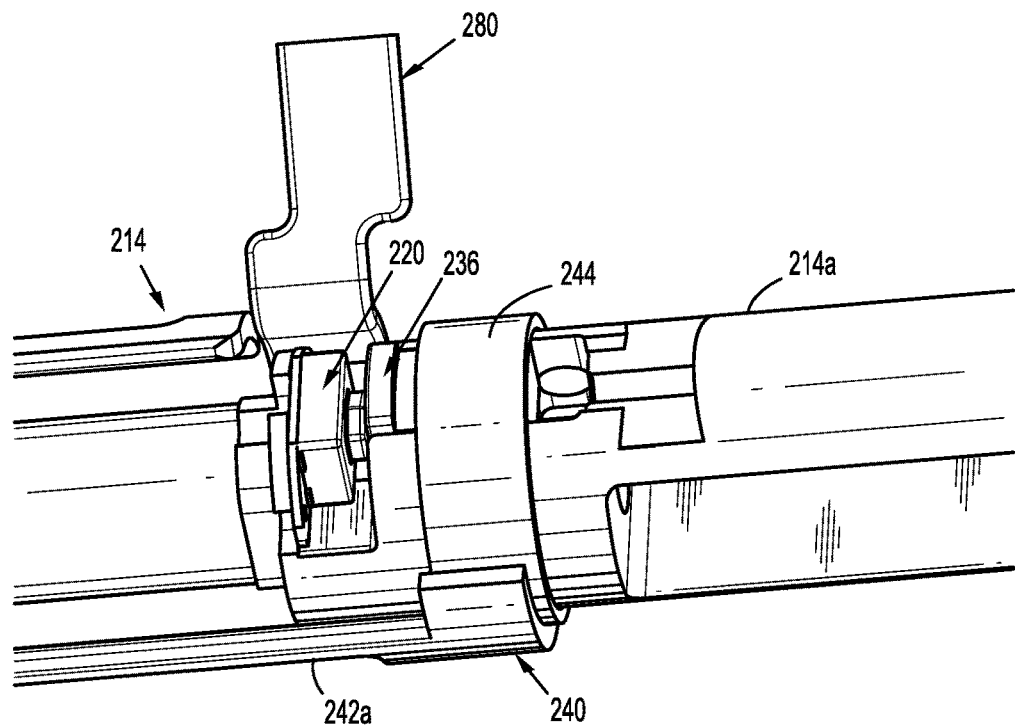
FIG. 7 is a perspective view of the proximal portion of the inner housing of FIG. 2, illustrating the switch, the pusher, and the switch actuator assembled therein.
Figure 12A:
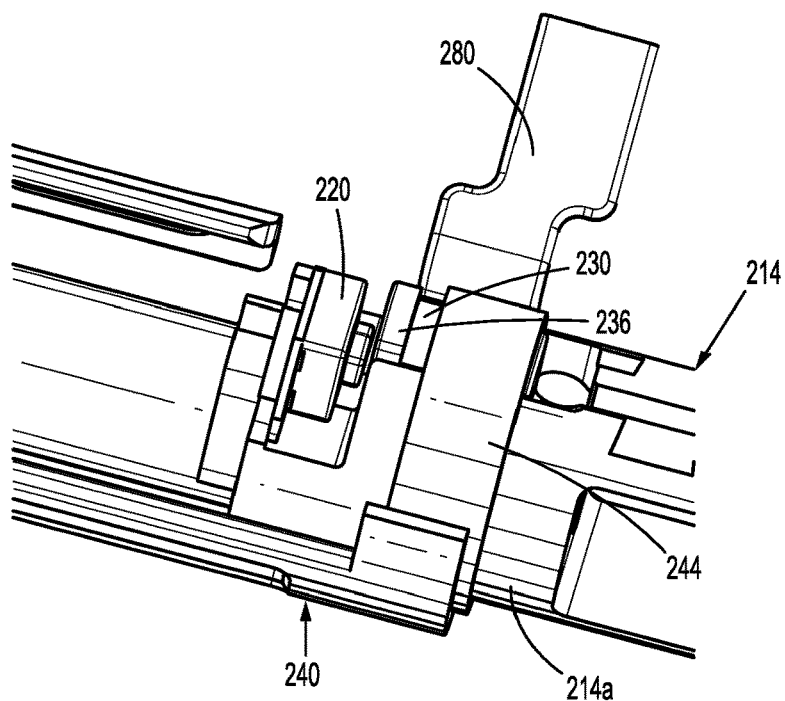
FIG. 12A is a perspective view of the proximal portion of the inner housing of FIG. 2, illustrating the switch in an unactuated state.
Figure 12B:
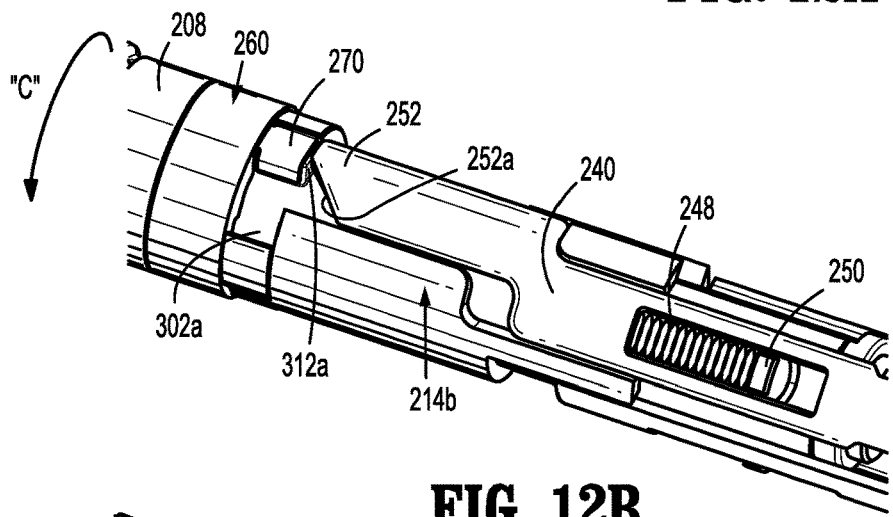
FIG. 12B is a perspective view of the distal portion of the adapter assembly of FIG. 1B engaged with the surgical loading unit of FIG. 1C, illustrating the annular member in a first orientation and the switch actuator in a proximal position.
Figure 12C:
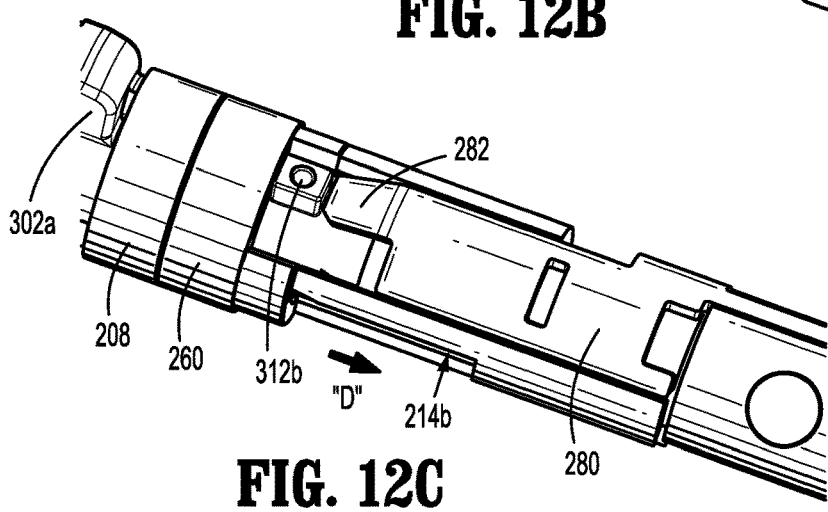
FIG. 12C is an alternate perspective view of the distal portion of the adapter assembly of FIG. 1B engaged with the surgical loading unit of FIG. 1C, illustrating the locking link in a non-locking configuration.
Figure 13A:
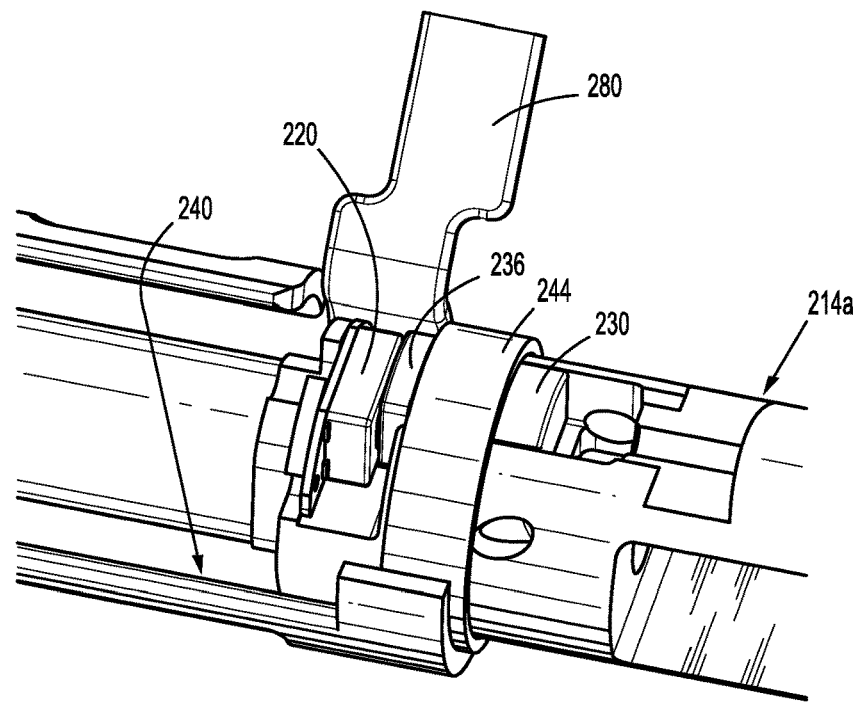
FIG. 13A is a perspective view of the proximal portion of the inner housing of FIG. 2, illustrating the switch in an actuated state.
Figure 13B:
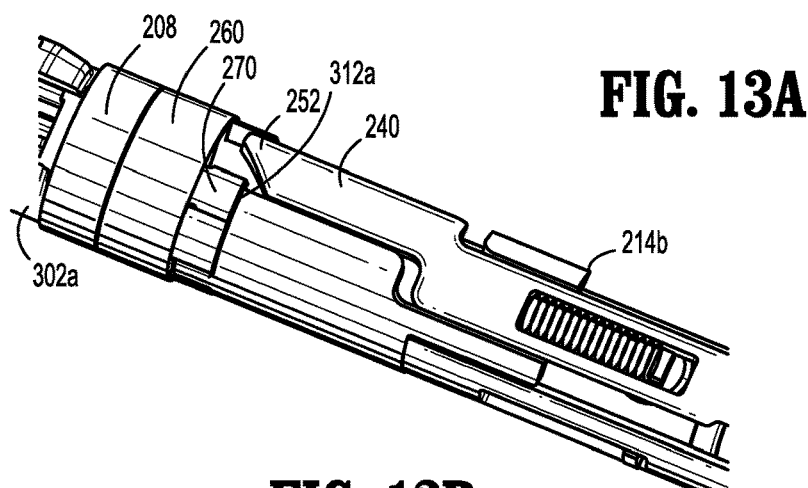
FIG. 13B is a perspective view of the distal portion of the adapter assembly of FIG. 1B lockingly coupled with the surgical loading unit of FIG. 1C, illustrating the annular member in a second orientation and the switch actuator in a distal position.

With reference to FIGS. 5-8, switch actuator 240 is slidingly disposed along inner housing 214 of elongated body 204. Specifically, switch actuator 240 is longitudinally movable relative to inner housing 214 between a proximal position, as shown in FIGS. 7, 12A, and 12B, and a distal position, as shown in FIGS. 4, 13A, and 13B. Switch actuator 240 toggles switch 220 during movement between proximal and distal positions. In embodiments, switch actuator 240 may actuate switch 220 when in the distal position or the proximal position depending on the orientation of the switch 220.

Switch actuator 240 has a proximal end 242a disposed adjacent switch 220 and a distal end 242b disposed adjacent distal portion 206b of elongated body 204. Proximal end 242a includes ring 244 attached thereto. Ring 244 encircles proximal portion 214a of inner housing 214 and is engaged to top surface 234b of pusher 230 such that pusher 230 is captured between ring 244 and inner housing 214, as best shown in FIG. 5. As ring 244 moves in a distal direction, as indicated by arrow "A" in FIG. 5, ring 244 abuts stepped portion 236 of pusher 230 to drive pusher 230 into engagement with switch 220, actuating, e.g., depressing, switch 220. As ring 244 moves in a proximal direction, indicated by arrow "B" in FIG. 5, a resilient bias of switch 220 oriented in the proximal direction drives pusher 230 in the proximal direction such that switch 220 enters an unactuated state. In some embodiments, ring 244 is frictionally engaged to pusher 230 such that movement of ring 244 moves pusher 230 in the proximal or distal directions.

Figure 8:
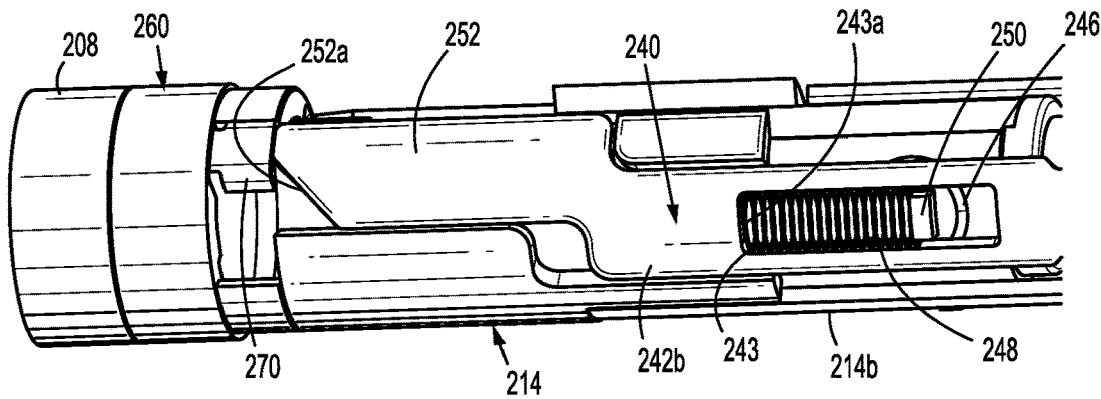
FIG. 8 is a perspective view of a distal portion of the inner housing of FIG. 2 and a distal portion of the switch actuator of FIG. 6.

With reference to FIGS. 6 and 8, distal end 242b of switch actuator 240 includes an inner surface 243 that defines an elongated opening 246 having a biasing member, such as, for example, a coil spring 248, disposed therein. Coil spring 248 is secured within opening 246 between a distal end 243a of inner surface 243 and a projection 250 of inner housing 214, which projects through opening 246. Coil spring 248 resiliently biases switch actuator 240 toward the distal position. Distal end 242b of switch actuator 240 includes an extension 252 having a tapered portion 252a. Extension 252 is in contact with an appendage 270 of annular member 260 when annular member 260 is in a selected orientation relative to extension 252, such that switch actuator 240 is maintained in the proximal position, as described in greater detail below.

Figure 9:
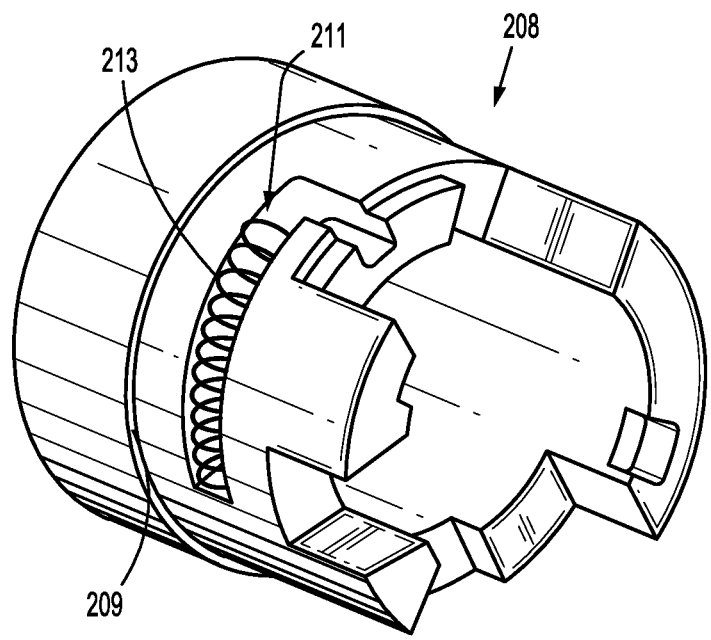
FIG. 9 is an enlarged view, with parts separated, of a distal tip of the inner housing of FIG. 2 and an annular member.
Figure 9:
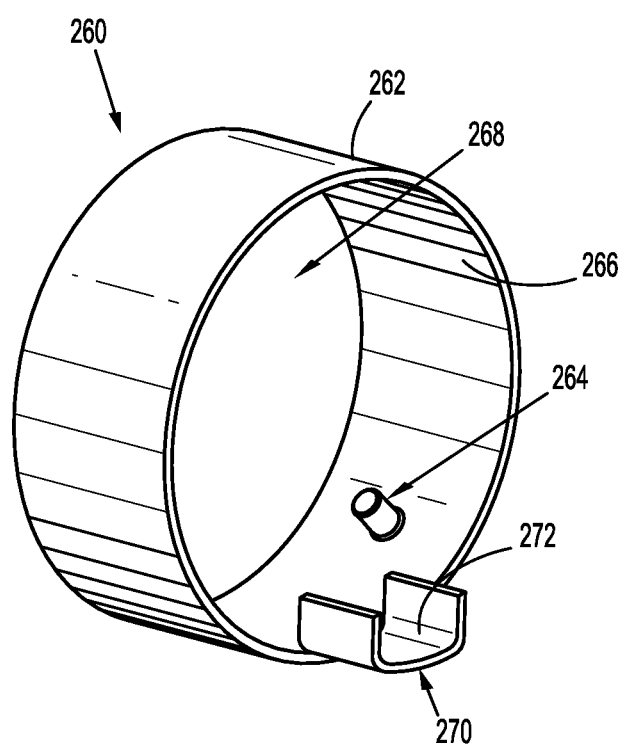

With reference to FIG. 9, annular member 260 is rotatably disposed around distal tip 208 of inner housing 214 and is captured between a ledge 209 of distal tip 208 and distal portion 206b of elongated body 204 (FIG. 1B). Distal tip 208 defines a slot 211 therein that extends circumferentially thereabout to define an arcuate pathway that orbits longitudinal axis "X" of elongated body 204. Annular member 260 includes a ring-shaped body 262. Ring-shaped body 262 has a protrusion or projection 264 extending from an inner surface 266 thereof into a passageway 268 defined through ring-shaped body 262. Projection 264 is movably positionable within slot 211 of distal tip 208. Distal tip 208 includes a biasing member, such as, for example, a spring 213, captured in slot 211. Upon assembly of annular member 260 with distal tip 208, spring 213 abuts projection 264 of annular member 260, which may be ring-shaped, to resiliently bias annular member 260 toward a first orientation relative to distal tip 208. In embodiments, one or more portions of annular member 260 may be ring-shaped.

Annular member 260 further includes an appendage 270 extending proximally from ring-shaped body 262. Appendage 270 of annular member 260 is configured to interface with a first surface feature or first lug 312a (FIG. 11) of loading unit 300, such that annular member 260 is rotatable by and with loading unit 300. Specifically, appendage 270 defines a cavity 272 therein having a rectangular cross-sectional configuration for mating engagement with correspondingly shaped first lug 312a of loading unit 300. In embodiments, cavity 272 may be of various shapes, such as, for example, triangular, circular, variable, tapered, polygonal, and the like. Cavity 272 is aligned with passageway 268 defined through ring-shaped body 262. Cavity 272 is shaped and dimensioned to capture first lug 312a (FIG. 11) of loading unit 300 upon insertion of loading unit 300 through passageway 268, such that annular member 260 is rotatable with and by loading unit 300. Appendage 270 of annular member 260 is also configured to abut extension 252 of switch actuator 240 to maintain switch actuator 240 in the proximal position when annular member 260 is in the first orientation.

Annular member 260 is rotatable between the first orientation and a second orientation. In the first orientation, appendage 270 of annular member 260 abuts extension 252 of switch actuator 240. In this configuration, appendage 270 prevents distal movement of switch actuator 240 from the proximal position to the distal position, thereby maintaining ring 244 of switch actuator 240 and pusher 230 out of engagement with switch 220. Accordingly, appendage 270 of annular member 260 has a dual function for both maintaining switch actuator 240 in the proximal position, out of engagement with switch 220, and for capturing first lug 312a of loading unit 300 in cavity 272 to provide an interface between loading unit 300 and annular member 260.

In use, loading unit 300 is inserted within the distal portion 206b of elongated body 204 and through passageway 268 of annular member 260 to mate first lug 312a of loading unit 300 with appendage 270 of annular member 260, as shown in FIG. 12B. Loading unit 300 is rotated, in a direction indicated by arrow "C" (FIG. 12B), to drive a rotation of annular member 260 from the first orientation to the second orientation, in so doing, overcoming the resilient bias of spring 213 of distal tip 208. Rotation of annular member 260 from the first orientation to the second orientation moves appendage 270 of annular member 260 out of a longitudinal pathway of extension 252 of switch actuator 240 such that coil spring 248 of switch actuator 240 biases switch actuator 240 toward the distal position, in which switch 220 is toggled, as shown in FIG. 13A.

Figure 10:
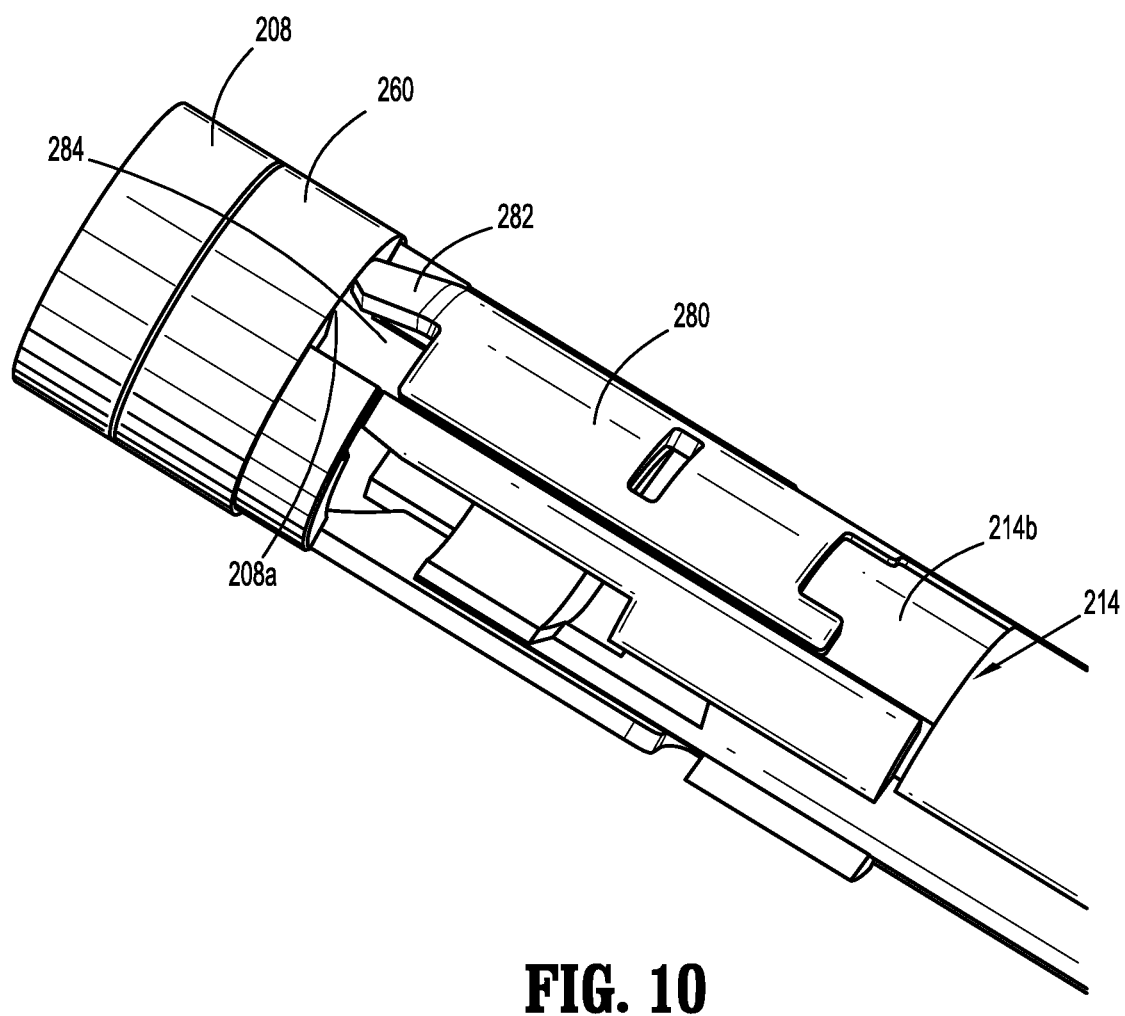
FIG. 10 is a perspective view of a locking link of the adapter assembly of FIG. 1B.
Figure 13C:
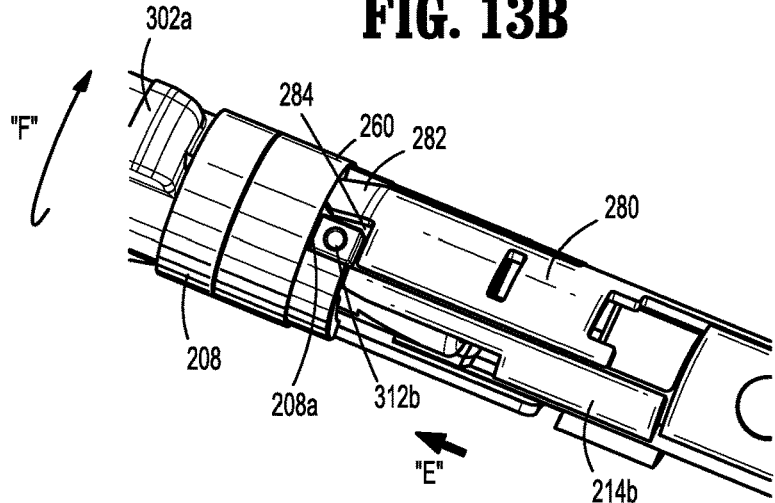
FIG. 13C is an alternate perspective view of the distal portion of the adapter assembly of FIG. 1B lockingly coupled with the surgical loading unit of FIG. 1C, illustrating the locking link in a locking configuration.

With reference to FIG. 10, locking link 280 is disposed within distal portion 206b of adapter assembly 200 and is configured to lockingly connect loading unit 300 with adapter assembly 200. Locking link 280 is slidingly disposed within or along inner housing 214 of adapter assembly 200 and is resiliently biased toward a locking configuration, as shown in FIGS. 10 and 13C. In the locking configuration, a distal end or bent extension 282 of locking link 280 is engaged with distal tip 208. Extension 282 of locking link 280 is configured for locking engagement with a second surface feature, such as, for example, a second lug 312b (FIG. 11) of loading unit 300 upon insertion and rotation of loading unit 300 into elongated body 204. As shown in FIG. 13C, in the locking configuration, second lug 312b of loading unit 300 is captured in an enclosure 284 defined by extension 282 of locking link 280 and distal tip 208.

Figure 11:
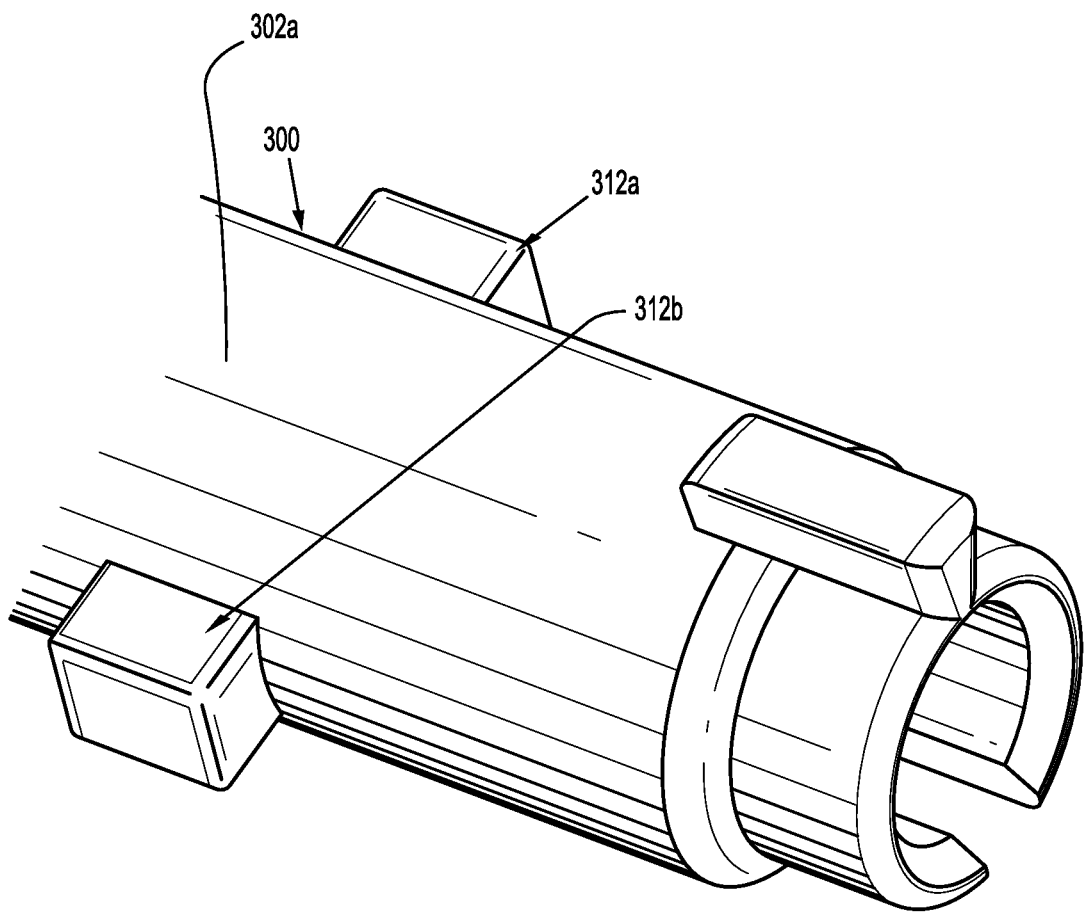
FIG. 11 is a perspective view of a proximal portion of the loading unit of FIG. 1C.

Turning to FIGS. 1C and 11, loading unit 300 of surgical instrument 10 has a proximal portion 302a configured for engagement with distal portion 206b of elongated body 204 of adapter assembly 200. Loading unit 300 includes a distal portion 302b having an end effector 304 extending therefrom. End effector 304 is pivotally attached to distal portion 302b. End effector 304 includes an anvil assembly 306 and a cartridge assembly 308. Cartridge assembly 308 is pivotable in relation to anvil assembly 306 and is movable between an open or unclamped position and a closed or clamped position for insertion through a cannula of a trocar.

Reference may be made to U.S. Pat. No. 7,819,896, filed on Aug. 31, 2009, entitled "TOOL ASSEMBLY FOR A SURGICAL STAPLING DEVICE", the entire contents of which are incorporated herein by reference, for a detailed discussion of the construction and operation of an exemplary end effector.

As briefly mentioned above, loading unit 300 further includes first and second lugs 312a, 312b each disposed on an outer surface of proximal end 302a of loading unit 300. First lug 312a has a substantially rectangular cross-section corresponding to cavity 272 of appendage 270 of annular member 260. Second lug 312b has a substantially rectangular cross-section corresponding to enclosure 284. Proximal end 302a of loading unit 300 is sized and dimensioned to be inserted through distal tip 208 and in turn, passageway 268 of annular member 260, to lockingly engage loading unit 300 with adapter assembly 200.

In operation, with reference to FIGS. 12A-C and 13A-C, a surgical loading unit, such as, for example, loading unit 300 of FIG. 1C, is inserted into distal portion 206b of elongated body 204 of adapter assembly 200 to matingly engage first lug 312a of loading unit 300 with appendage 270 of annular member 260, as shown in FIG. 12B. The insertion of loading unit 300 within adapter assembly 200 also engages second lug 312b of loading unit 300 with extension 282 of locking link 280 to move locking link 280 in a proximal direction, as shown by arrow "D" in FIG. 12C, to the non-locking configuration. With loading unit 300 in this initial insertion position within adapter assembly 200, switch actuator 240 remains in the proximal position out of engagement with switch 220.

To lockingly engage loading unit 300 with adapter assembly 200, loading unit 300 is rotated, in a direction indicated by arrow "C," to drive a rotation of annular member 260, via the mating engagement between first lug 312a of loading unit 300 and appendage 270 of annular member 260, from the first orientation to the second orientation. The rotation of annular member 260 from the first orientation to the second orientation displaces appendage 270 of annular member 260 away from extension 252 of switch actuator 240. With appendage 270 out of a longitudinal pathway of extension 252 of switch actuator 240, switch actuator 240 moves from the proximal position, as shown in FIG. 12A, to the distal position, as shown in FIG. 13B, via the resilient bias of coil spring 248. As switch actuator 240 moves to the distal position, ring 244 of switch actuator 240 moves/slides/translates pusher 230 in a distal direction such that pusher 230 toggles switch 220, e.g., by depressing switch 220, as shown in FIG. 13A. Depressing or actuating switch 220 communicates to handle assembly 100 that loading unit 300 is lockingly engaged with adapter assembly 200 and is ready for operation.

The rotation of loading unit 300 also moves second lug 312b of loading unit 300 into an inner groove 208a defined in distal cap 208 and out of a longitudinal pathway of extension 282 of locking link 280. The resilient bias of locking link 280 drives an axial translation of locking link 280, in a direction indicated by arrow "E" in FIG. 13C, to position locking link 280 in the locking configuration. With locking link 280 in the locking configuration, second lug 312b of loading unit 300 is captured within enclosure 284 defined by extension 282 of locking link 280 and inner groove 208a of distal cap 208. Loading unit 300 is prevented from moving distally out of enclosure 284 due to inner groove 208a, and is prevented from rotating, in a direction indicated by arrow "F" shown in FIG. 13C, due to extension 282 of locking link 280. Therefore, loading unit 300 is releasably, lockingly engaged to adapter assembly 200.

To selectively release loading unit 300 from adapter assembly 200, a surgeon or clinician translates or pulls locking link 280 in a proximal direction, such that extension 282 of locking link 280 is no longer blocking a rotational pathway of second lug 312b of loading unit 300 and loading unit 300 can be rotated. Loading unit 300 is rotated, in the direction indicated by arrow "F," to move second lug 312b of loading unit 300 out of abutment with inner groove 208a of distal cap 208. The rotation of loading unit 300 also drives the rotation of annular member 260 from the second orientation to the first orientation via the mating engagement of first lug 312a of loading unit 300 and appendage 270 of annular member 260. As annular member 260 rotates, appendage 270 rides along tapered portion 252a of extension 252 of switch actuator 240 to drive switch actuator 240 in a proximal direction until annular member 260 is in the first orientation and switch actuator 240 is in the proximal position, out of engagement with switch 220. Specifically, proximal movement of switch actuator 240 allows pusher 230 to move proximally, out of engagement with switch 220, via the proximally-oriented resilient bias of switch 220. Upon pusher 230 of switch actuator 240 disengaging switch 220, switch 220 is toggled, which communicates to handle assembly 100 that loading unit 300 is no longer lockingly engaged with adapter assembly 200 and not ready for operation.

To fully disengage loading unit 300 from adapter assembly 200, loading unit 300 is axially translated, in a distal direction, through passageway 268 (FIG. 9) of annular member 260 and through distal cap 208, out of elongated body 204 of adapter assembly 200. It is contemplated that upon handle assembly 100 detecting that loading unit 300 is not lockingly engaged to adapter assembly 200, power may be cut off from handle assembly 100, an alarm (e.g., audio and/or visual indication) may be issued, or combinations thereof.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

The invention claimed is:

1. An adapter assembly, comprising:
   an elongated body including a proximal portion configured to couple to a handle assembly and a distal portion configured to couple to a surgical loading unit;
   a switch disposed within the elongated body;
   a sensor link having a proximal end disposed adjacent the switch and a distal end disposed adjacent the distal portion of the elongated body, the sensor link being longitudinally movable between a proximal position and a distal position; and
   an annular member disposed within the distal portion of the elongated body and being rotatable between a first orientation, in which the annular member prevents movement of the sensor link to the distal position, and a second orientation, in which the sensor link is movable from the proximal position to the distal position to toggle the switch, the annular member being resiliently biased toward the first orientation.

2. The adapter assembly according to claim 1, wherein the distal portion of the elongated body defines a slot therein and the annular member includes a protrusion movably disposed within the slot.

3. The adapter assembly according to claim 2, wherein the distal portion of the elongated body includes a biasing member disposed within the slot and in abutment with the protrusion of the annular member.

4. The adapter assembly according to claim 3, wherein the slot of the elongated body extends circumferentially about the distal portion thereof.

5. The adapter assembly according to claim 1, wherein the annular member includes an appendage defining a cavity therein configured to capture a surface feature of the surgical loading unit.

6. The adapter assembly according to claim 5, wherein the appendage abuts the distal end of the sensor link when the annular member is in the first orientation such that the appendage maintains the sensor link in the proximal position.

7. The adapter assembly according to claim 1, wherein the elongated body defines a longitudinal channel within the proximal portion, the adapter assembly further comprising a pusher movably disposed within the longitudinal channel.

8. The adapter assembly according to claim 7, wherein the proximal end of the sensor link is in engagement with the pusher such that movement of the sensor link toward the distal position moves the pusher to actuate the switch.

9. The adapter assembly according to claim 8, wherein the pusher includes a stepped portion and the proximal end of the sensor link includes a ring abutting the stepped portion such that movement of the ring moves the pusher.

10. The adapter assembly according to claim 1, wherein the sensor link is resiliently biased toward the distal position.

11. The adapter assembly according to claim 1, further comprising a locking link disposed within the elongated body, the locking link including an extension configured for locking engagement with a lug of the surgical loading unit, the locking link being resiliently biased to secure the surgical loading unit to the distal portion of the elongated body upon insertion and rotation of the surgical loading unit into the elongated body.

12. A surgical instrument, comprising:
a handle assembly including a processor configured to control a motor;
a surgical loading unit having a proximal end and a distal end, the proximal end having a surface feature and the distal end having an end effector; and
an adapter assembly including:
an elongated body including a proximal portion configured to couple to the handle assembly and a distal portion configured to couple to the surgical loading unit, the distal portion defining a slot therein;
a switch disposed adjacent the proximal portion of the elongated body;
a sensor link having a proximal end disposed adjacent the switch and a distal end disposed adjacent the distal portion of the elongated body, the sensor link being longitudinally movable between a proximal position and a distal position; and
an annular member having a protrusion movably disposed within the slot of the elongated body, the annular member being rotatable between a first orientation, in which the annular member prevents movement of the sensor link to the distal position, and a second orientation, in which the sensor link is movable from the proximal position to the distal position to toggle the switch, the annular member being resiliently biased toward the first orientation.

13. The surgical instrument according to claim 12, wherein the slot of the elongated body extends circumferentially about the distal portion of the elongated body and the distal portion of the elongated body includes a biasing member disposed within the slot and in abutment with the protrusion of the annular member.

14. The surgical instrument according to claim 12, wherein the annular member includes an appendage configured to capture the surface feature of the loading unit such that rotation of the loading unit rotates the annular member between the first and second orientations.

15. The surgical instrument according to claim 14, wherein the appendage abuts the distal end of the sensor link when the annular member is in the first orientation such that the appendage maintains the sensor link in the proximal position.

16. The surgical instrument according to claim 12, wherein the sensor link is resiliently biased toward the distal position.

17. The surgical instrument according to claim 16, further comprising a pusher movably disposed within a longitudinal channel defined in the proximal portion of the elongated body, wherein the proximal end of the sensor link is in engagement with the pusher such that movement of the sensor link toward the distal position moves the pusher to actuate the switch.

18. The surgical instrument according to claim 17, wherein the pusher includes a stepped portion and the proximal end of the sensor link includes a ring abutting the stepped portion such that movement of the ring moves the pusher.

19. The surgical instrument according to claim 12, further comprising a locking link disposed within the elongated body, the locking link including an extension configured for locking engagement with a lug of the surgical loading unit, the locking link being resiliently biased to secure the surgical loading unit to the distal portion of the elongated body upon insertion and rotation of the surgical loading unit into the elongated body.

20. The surgical instrument according to claim 12, wherein the processor is configured to activate the motor upon the switch being toggled.

* * * * *